(12) United States Patent
Ginther (10) Patent No.: US 9,594,062 B2
(45) Date of Patent: Mar. 14, 2017

(54) SYSTEM AND METHOD FOR TESTING TRANSDUCER ELEMENTS OF AN ACOUSTIC PROBE

(71) Applicant: GENERAL ELECTRIC COMPANY, Schenectady, NY (US)

(72) Inventor: James Ginther, Boulder, CO (US)

(73) Assignee: General Electric Company, Schenectady, NY (US)

( * ) Notice: Subject to any disclaimer, the term of this patent is extended or adjusted under 35 U.S.C. 154(b) by 256 days.

(21) Appl. No.: 14/499,734

(22) Filed: Sep. 29, 2014

(65) Prior Publication Data

US 2016/0091466 A1 Mar. 31, 2016

(51) Int. Cl.
*G01N 29/30* (2006.01)
*G01N 29/24* (2006.01)
*G01M 99/00* (2011.01)

(52) U.S. Cl.
CPC .......... *G01N 29/30* (2013.01); *G01M 99/008* (2013.01); *G01N 2291/106* (2013.01)

(58) Field of Classification Search
CPC .......... G01M 99/008; G01N 2291/106; G01N 29/24; G01N 29/30
See application file for complete search history.

(56) References Cited

U.S. PATENT DOCUMENTS

| | | |
|---|---|---|
| 4,240,281 A | 12/1980 | Lather et al. |
| 5,517,994 A | 5/1996 | Burke et al. |
| 6,920,776 B2 | 7/2005 | Gessert et al. |
| 6,928,856 B2 | 8/2005 | Gessert et al. |
| 7,007,539 B2 | 3/2006 | Gessert et al. |
| 7,028,529 B2 | 4/2006 | Gessert et al. |
| 7,155,957 B2 | 1/2007 | Gessert et al. |
| 7,246,264 B2 | 7/2007 | Grellmann et al. |
| 7,266,987 B2 | 9/2007 | McCartan et al. |
| 7,272,762 B2 | 9/2007 | Horwath et al. |
| 7,278,289 B2 | 10/2007 | Gessert et al. |
| 7,726,172 B2 | 6/2010 | Moore et al. |
| 7,880,488 B2 | 2/2011 | Dananay et al. |

(Continued)

FOREIGN PATENT DOCUMENTS

| | | |
|---|---|---|
| EP | 1837681 A2 | 9/2007 |
| WO | 2011017646 A1 | 2/2011 |

OTHER PUBLICATIONS

Great Brittan office action issued in connection with corresponding GB Application No. GB1515969.2 on Feb. 8, 2016.

*Primary Examiner* — Francis Gray (57) ABSTRACT

A system and method for testing an acoustic probe having a series of transducer elements adapted to convert between acoustic and electrical signals is provided. The system comprises an acoustic signal generator and a receiver. The acoustic signal generator sends an acoustic signal into at least one of the series of transducer elements of the acoustic probe. An electrical transducer signal generated in response to receipt of the acoustic signal at the selected transducer element. The receiver has a switch to receive the electrical transducer signal from each selected transducer element of the acoustic probe. A display provides an illustration indicative of an operative ability of the selected transducer element of the acoustic probe to convert between acoustic and electrical signals.

20 Claims, 3 Drawing Sheets

(56) References Cited

U.S. PATENT DOCUMENTS

| | | | |
|---|---|---|---|
| 8,001,843 B2 * | 8/2011 | Yao | A61B 8/54 |
| | | | 73/609 |
| 8,008,906 B2 | 8/2011 | Valenti, III | |
| 8,100,015 B2 * | 1/2012 | Karasawa | G01N 29/226 |
| | | | 73/602 |
| 8,159,900 B2 | 4/2012 | Moore et al. | |
| 8,164,976 B2 | 4/2012 | Moore et al. | |
| 8,169,853 B2 | 5/2012 | Moore et al. | |
| 8,199,920 B2 | 6/2012 | Valenti, III | |
| 8,215,152 B2 | 7/2012 | Kim | |
| 2011/0307181 A1 * | 12/2011 | Nagae | G01S 7/52047 |
| | | | 702/19 |
| 2011/0319743 A1 * | 12/2011 | Satoh | A61B 5/0095 |
| | | | 600/407 |
| 2012/0256646 A1 | 10/2012 | Ginther et al. | |
| 2012/0271573 A1 | 10/2012 | Markoff et al. | |
| 2013/0283916 A1 | 10/2013 | Hersey et al. | |
| 2013/0312528 A1 * | 11/2013 | Feydo | G01N 29/262 |
| | | | 73/632 |
| 2014/0020469 A1 | 1/2014 | Gessert et al. | |

* cited by examiner

SYSTEM AND METHOD FOR TESTING TRANSDUCER ELEMENTS OF AN ACOUSTIC PROBE

TECHNICAL FIELD

The subject herein generally relates to a system and method to test an acoustic probe, and more specifically to a system and method to test operability of the transducer elements of an acoustic probe to convert between acoustic and electrical signals.

BACKGROUND

The statements in this section merely provide background information related to the disclosure and may not constitute prior art.

Acoustic imaging techniques have been found to be valuable in a variety of applications. A certain acoustic imaging technique referred to as ultrasound imaging is perhaps the most well-known, but acoustic techniques are more generally used at a variety of different acoustic frequencies for imaging a variety of different phenomena. Certain acoustic imaging techniques use transmission and detection of acoustic radiation in identification of structural defects, detection of impurities, as well as detection of tissue abnormalities in living bodies. All such acoustic imaging techniques rely generally on the fact that different structures, whether they are abnormal bodily tissues or defects in an airplane wing, have different impedances to acoustic radiation. Certain known acoustic imaging systems include an acoustic probe having multiple-element array transducer elements that may have linear, curved-linear, phased-array, or similar characteristics to control the transmission and detection of acoustic radiation. Degradation in performance of such transducer elements is known to occur with extended transducer use and/or through user abuse. Certain known techniques to test the degradation of the transducer elements require the use of a reflective target and a tank of water as a conductive medium in order to analyze the performance of such transducer elements. A drawback of such acoustic testing techniques includes the difficulty in alignment of the acoustic probe with respect to the water tank and target, such difficulty encumbering the speed and repeatability of the acoustic test.

There is, therefore, a general need in the art for a system and method of testing acoustic probes that requires less infrastructure (i.e., target and water tank) and yet improves speed and repeatability of the test of the operability of the acoustic probe.

BRIEF SUMMARY

In view of the above concerns associated with use of ionizing radiation, there is a need for systems, methods and computer program products that provides for a quick and repeatable test of the operative ability of the acoustic probe that does not require use of certain cumbersome infrastructure such as an acoustic target or a water tank as a conductive medium. The above-described needs are addressed by the embodiments of the subject matter described herein.

One aspect of the subject matter includes a system for testing an acoustic probe having a series of transducer elements adapted to convert between acoustic and electrical signals. The system comprises an acoustic signal generator and a receiver. The acoustic signal generator sends an acoustic signal into at least one of the series of transducer elements of the acoustic probe. An electrical transducer signal generated in response to receipt of the acoustic signal at the selected transducer element. The receiver has a switch to receive the electrical transducer signal from each selected transducer element of the acoustic probe. A display provides an illustration indicative of an operative ability of the selected transducer element of the acoustic probe to convert between acoustic and electrical signals.

According to another aspect, a method of testing an acoustic probe having a series of transducer elements adapted for conversion between acoustic and electrical signals is provided. The method comprises the steps of: sending an acoustic signal into at least one of the series of transducer elements of the acoustic probe; detecting receipt of an electrical transducer signal via a switch at a receiver from each selected transducer element of the acoustic probe, the electrical transducer signal generated in response to receipt of the acoustic signal at the selected transducer element; displaying an indication of the operative ability of the selected transducer element of the acoustic probe to respond to the acoustic signal in response to the detecting step.

According to yet another aspect, a non-transitory, tangible, computer-readable storage medium having a computer-readable program embodied therein is provided. The computer-readable program is for directing operation of a system including an acoustic signal generator, and a receiver having a switch. The computer readable program includes instructions for operation in determining an operability of each of a plurality of transducer elements adapted for conversion between acoustic and electrical signals with respect to operation of an acoustic probe in accordance with the following: sending an acoustic signal into at least one of the plurality of transducer elements of the acoustic probe; detecting receipt of an electrical transducer signal via a switch at a receiver from each selected transducer element of the acoustic probe, the electrical transducer signal generated in response to receipt of the acoustic signal at the selected transducer element; and creating a display indicative of the operative ability of the selected transducer element of the acoustic probe to respond to the acoustic signal in response to the detecting step.

This summary briefly describes aspects of the subject matter described below in the Detailed Description, and is not intended to be used to limit the scope of the subject matter described in the present disclosure.

BRIEF DESCRIPTION OF THE DRAWINGS

The features and technical aspects of the system and method disclosed herein will become apparent in the following Detailed Description in conjunction with the drawings in which reference numerals indicate identical or functionally similar elements.

DETAILED DESCRIPTION

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. The term user and/or the plural form of this term is used to generally refer to those persons capable of accessing, using, or benefiting from the present disclosure. As used herein, when the phrase "at least" is used, it is open-ended in the same manner as the term "comprising" is open-ended.

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
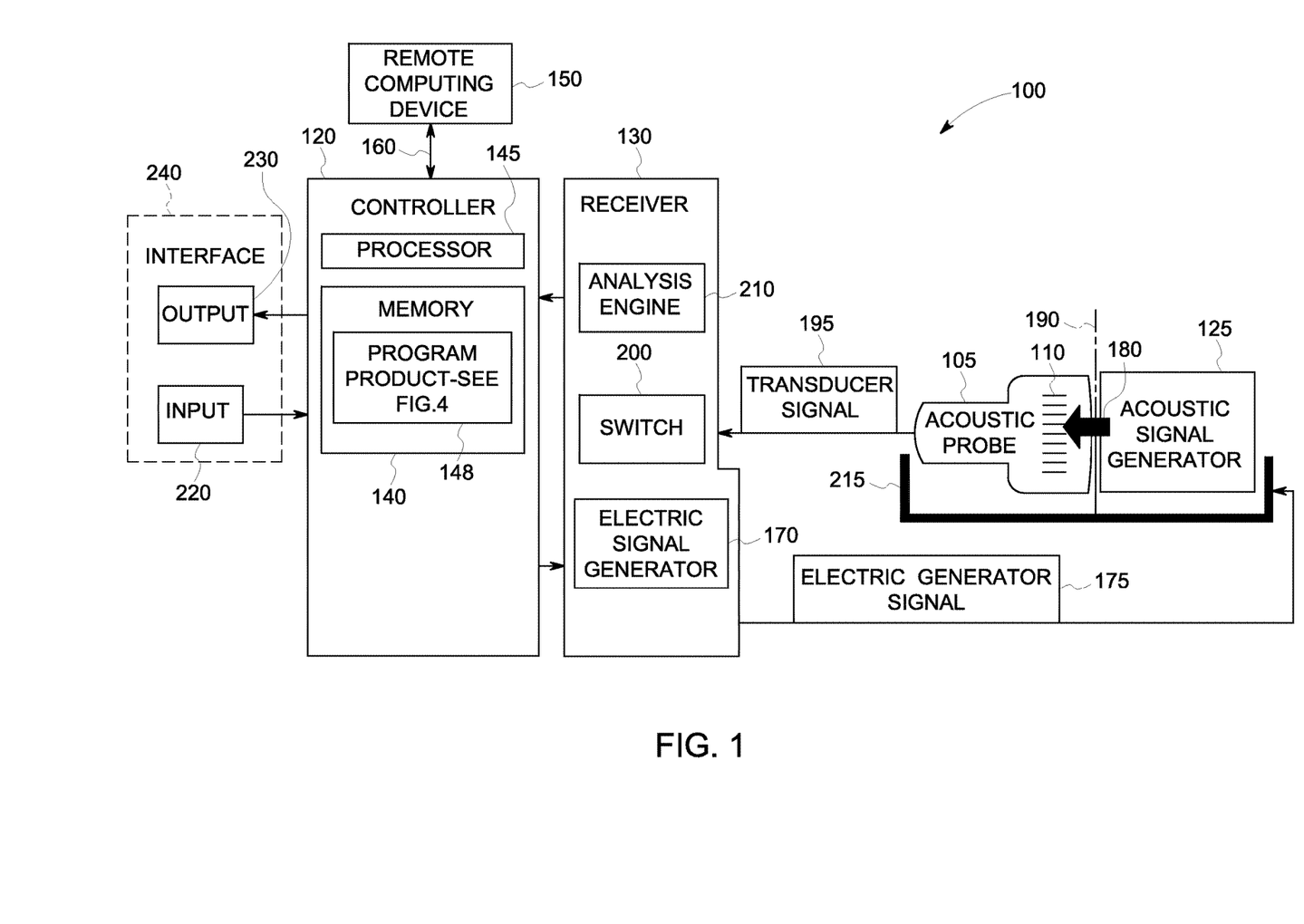
FIG. 1 shows a schematic block diagram of an example of a system in accordance to the subject matter described herein.

FIG. 1 illustrates one embodiment of a system 100 for testing an acoustic probe 105 having a series of transducer elements (shown schematically by lines) 110 adapted to convert between acoustic and electrical signals. In general, the system 100 comprises a controller 120 connected to communicate with an acoustic signal generator 125 and a receiver 130 in testing of the acoustic probe 105. Each transducer element 110 of the acoustic probe 105 generally includes a piezoelectric crystal (not shown) constructed to convert between acoustic and electrical signals and a lens (not shown) to focus generated acoustic energy in measurement of an impedance of structures (e.g., bodily tissue, etc.). In particular, the piezoelectric crystals are known in the art to convert received electric signals to acoustic radiation or signals for emission, as well as to convert incident acoustic radiation back to electrical signals for translation into images indicative of the material of the incident structure.

The controller 120 of the system 100 is generally operative to receive, process, and convey information to and from the acoustic signal generator 125 and the receiver 130. The example of the controller 120 can generally include a memory 140 having a series of computer readable program instructions for execution by a computer or hardware processor (herein "computer processor") 145. The example memory 140 can include or be a non-transitory, tangible, computer program product 148 of varying type generally operable to store electronic formatted data or information and program instructions accessible and readable by the computer processor 145. In certain examples, the memory 140 can be accessible by a remote computing device 150 via the network connection 160.

The computer-readable instructions can comprise a programming code for execution by the computer processor 145. The programming code can be embodied in software stored on the memory 140 independent of or in combination with software embodied in firmware or dedicated hardware. The computer program product 148 can include a computer-readable storage medium that is tangible, non-transitory, and having volatile and non-volatile, and removable and non-removable media for storage of electronic-formatted information such as computer readable program instructions or modules of instructions, data, etc. that may be stand-alone or as part of the controller 120. As used herein, the term tangible, non-transitory computer readable storage medium can be expressly defined to include any type of computer readable storage device and/or storage disk and to exclude propagating signal media and to exclude transmission media. As used herein, "tangible computer readable storage medium" and "tangible machine readable storage medium" can be used interchangeably.

Examples of the memory 140 can include, but are not limited to, random access memory (RAM), read only memory (ROM), Synchronous Dynamic Random Access Memory (SDRAM), Dynamic Random Access Memory (DRAM), EEPROM, flash memory, a cache, compact disc (CD), digital versatile disc (DVD) or other optical storage, magnetic cassettes, magnetic tape, magnetic disk storage or other magnetic storage devices, a hard drive, a flash memory, or any other medium which can be used to store the desired electronic format of information or program instructions for a duration and which can be accessed by the computer processor 145 or at least a portion of the controller 120.

The example computer processor 145 can include hardware to execute one or more tasks as defined by the computer readable program instructions. The computer processor 145 can be, for example, part of a computer server, a laptop or desktop, a mobile device (e.g., a cell phone, a smart phone, a tablet such as an IPAD™), a personal digital assistant (PDA), an Internet appliance, or any other type of known computing device. For example, the computer processor 145 can be implemented by one or more integrated circuits, logic circuits, microprocessors or controllers from any desired family or manufacturer.

The memory 140 and computer processor 145 as referred to herein can be stand-alone or integrally constructed as part of various programmable computing devices of various types, including for example a cache, a desktop computer or laptop computer hard-drive, field-programmable gate arrays (FPGAs), application-specific integrated circuits (ASICs), application-specific standard products (ASSPs), system-on-a-chip systems (SOCs), programmable logic devices (PLDs), etc. or the like and any combination thereof operable to execute the instructions associated with implementing the method (discussed later) of the subject matter described herein.

The controller 120 can be connected to an electrical signal generator 170 in a manner to instruct the electrical signal generator 170 to communicate an electrical generator signal 170 at a predefined or input instructed frequency so as to trigger transmission of an acoustic signal 180 from the acoustic generator 125 at a desired frequency. An example of the electrical signal generator 170 can an alternating voltage source operable to generate an analog or digital signal in a radio frequency (RF) range.

The acoustic signal generator 125 can be generally operable to send or communicate the acoustic signal 180 into at least one of the series of transducer elements 110 of the acoustic probe 105. Acoustic signal 180 is generally defined as a pressure wave of propagating rarefactions and compressions through a medium and of a certain range (e.g., above an audible range of the human ear) generated by mechanical motion. As an example, the acoustic signal generator 125 can be configured to generate the acoustic signal 180 at a frequency defined by the received electrical signal from the electrical signal generator 170. An example of the desired frequency can be a frequency that includes a resonant frequency associated with the piezoelectric crystals of the transducer elements 110 of the acoustic probe 105 undergoing testing. The acoustic signal generator 125 can be configured to include a material (shown by dashed line and reference 190) such as a gel that enhances contact of the acoustic signal generator 125 against the acoustic probe 105 to be tested in a manner that enhances the transmission of the acoustic signal 180 into the transducer elements 110 of the acoustic probe 105.

In response to receipt of the transmitted acoustic signal 180 from the acoustic generator 125, properly operative transducer elements 110 respond with generation and transmission of an electrical transducer signal 195. In particular with respect to transducer elements 110 that comprise piezoelectric elements, transducer elements 110 impacted by receipt of the acoustic signal 180 can respond with generation of an electrical transducer signal (e.g., variable voltage signal) 195 in accordance to the piezoelectric effect. The receiver 130 of the system 100 is connected in communication with the acoustic probe 105 to receive the electrical transducer signals 195 generated in response to the transmission of the acoustic signal 180 into the acoustic probe 105 being tested.

The receiver 130 can include a switch 200 to receive the electrical transducer signal 195 from each selected transducer element 110 of the acoustic probe 105 in a desired manner. For example, the switch 200 can control selective communication or operational connections with one or a group of the transducer elements. An example of the switch 200 can be a relay matrix configured to establish connections in a desired sequential manner with the plurality of transducer elements 110 of the acoustic probe 105, either individually or in groups, that permits selective evaluation of individual or multiple transducer elements 110 of the acoustic probe 105. The relay matrix can comprise a bidirectional switching array capable of establishing the desired connections. The electrical characteristics of the relay matrix can be configured not to impact the evaluation of the transducer elements 110 of the acoustic probe 105. For example, the switch 200 can include an array of miniature relays, or a semiconductor-based switching integrated circuitry. In regard to the array of relays, the array of relays may be arranged in groups and in various circuit topologies to enhance transmission of the electrical transducer signals 195 under a constant electrical load.

Further, the receiver 130 can include an analysis engine 210 configured to detect receipt of the electrical transducer signal from the selected transducer element. An example of the analysis engine 210 can include a computational circuitry configured to compare predefined parameters of the received electrical transducer signal from the selected transducer element relative to a threshold. Examples of the parameters can include amplitude, frequency, etc. of the signal. Examples of the threshold can be predefined or based on benchmark values from measurements from other transducer elements 110 of the acoustic probe 105 being tested. The analysis engine 210 can further include an amplifier, an analog-to-digital converter, etc. to filter and process the electrical transducer signal for analysis. In one example, the analysis engine 210 can provided by a personal computer, a mainframe, or a laptop, whose mobility makes it especially convenient. Although FIG. 1 shows the analysis engine 210 as integrated with receiver 130, the analysis engine 210 can include computer program instructions or circuitry or combination thereof locas as part of the controller 120 or receiver 130 or combination thereof.

The system 100 can further include a holder 215 to secure the acoustic probe 105 during testing. The acoustic probe 105 can be secured to maintain or allow selective engagement of the acoustic signal generator 125 against or in contact with acoustic probe 105 so as to provide for transmission of the acoustic signal 180 from the acoustic signal generator 125 into the transducer elements 110 of the acoustic probe 105 being tested in a selective manner. The holder 215 can be equipped with adjustment capabilities, permitting, for example, selective angular orientation of the acoustic probe 105 in relation to the acoustic signal generator 125.

The controller 120 of the system 100 can also be configured to communicate instructions to and from the remote computer devices 150. Examples of remote computer devices 150 as referenced herein can include: a mobile telephone; a computer such as a desktop or laptop type; a Personal Digital Assistant (PDA) or mobile phone; a notebook, tablet or other mobile computing device; or the like and any combination thereof. The subject matter of this description may be implemented as a stand-alone computer program product or as an application configured for execution by one or more of the remote computing devices 150. The application (e.g., webpage, downloadable applet or other mobile executable) can generate the various displays or graphic/visual representations described herein as graphic user interfaces (GUIs) or other visual illustrations, which may be generated as webpages or the like, in a manner to facilitate interfacing (receiving input/instructions, generating graphic illustrations) with users via the remote computing device(s) 150.

A network 160 can facilitate transmission of electronic or digital data to and from the system 100 with respect to the remote computer devices 150. The example network 160 can be a wired interface (e.g., a data bus, a Universal Serial Bus (USB 2.0 or 3.0) connection, etc.) and/or a wireless interface (e.g., radio frequency, infrared, optical, near field communication (NFC), etc.), a wide area network (WAN); a local area network (LAN); the Internet; a cloud-based computing infrastructure of computers, routers, servers, gateways, etc.; or any combination thereof associated therewith that allows the system 100 or portion thereof to communicate with various computing devices 150 described above. With respect to the example of the network 160 as including a cloud-based infrastructure, the system 100 can share information via web-based applications, cloud storage and cloud services. For example, a Web-based portal may be used to facilitate access to information, etc. The system 100 can illustrate the Web-based portal as a central interface to access information and applications, and data may be viewed through the Web-based portal or viewer, for example. Additionally, data may be manipulated and propagated using the Web-based portal, for example. The Web-based portal can be accessible locally (e.g., in an office) and/or remotely (e.g., via the Internet and/or other network or connection 160), for example.

The controller 120 can also be in communication with an input or input device 220 and an output or output device 230. Examples of the input device 220 include a keyboard, joystick, mouse device, touch-screen, pedal assemblies, track ball, light wand, voice control, or similar known input device known in the art. Examples of the output device 230 include a liquid-crystal monitor, a plasma screen, a cathode ray tube monitor, a touch-screen, a printer, audible devices, etc. The input device 220 and output device 230 can be independent of one another, or combination as an interface 240 to the system 100.

Having provided an example of one construction of the system 100 as shown in FIG. 1 in accordance with above-description, the following is a description of an example of a method 300 (See FIG. 2) to operate the system 100 in accordance with the subject matter described herein. It should also be understood that the sequence of the acts or steps of the method 300 as discussed in the foregoing description can vary. Also, it should be understood that the method 300 may not require each act or step in the foregoing description, or may include additional acts or steps not disclosed herein. It should also be understood that one or more of the steps of the method 300 can be represented by one or more computer program modules of computer-readable program instructions stored in the memory 140 of the system 100. As mentioned above, the method 300 can be implemented using coded instructions (e.g., computer and/or machine readable instructions). The terms module and component as referenced herein can generally represent program code or instructions that causes specified tasks when executed on the computer processor 145. The program code can be stored in one or more computer readable mediums that comprise the memory 140 and computer program product 148.

For sake of example an referring to FIG. 1, assume during testing, the acoustic probe 105 can be secured by the holder 215 to maintain or allow selective engagement of the acoustic signal generator 125 against the acoustic probe 105 to be tested in a manner that provides transmission of the acoustic signal 180 from the acoustic signal generator 125 into the transducer elements 110 of the acoustic probe 105 for testing.

Referring again to FIG. 2, step 310 can include instructing the electrical signal generator 170 to trigger the acoustic signal generator 125. For example, the electrical generator signal 175 can be a voltage pulse. In response to the electrical signal in step 310, step 315 can include transmitting the acoustic signal 180 into the transducer elements 110 of the acoustic probe 105 being tested. The system 100 can be engaged with the acoustic probe 105 such that the transmitted acoustic signal 180 excites all or a portion of the transducer elements 110 of the acoustic probe 105 to convert the acoustic signal 180 to the electrical transducer signal 195.

Figure 2:
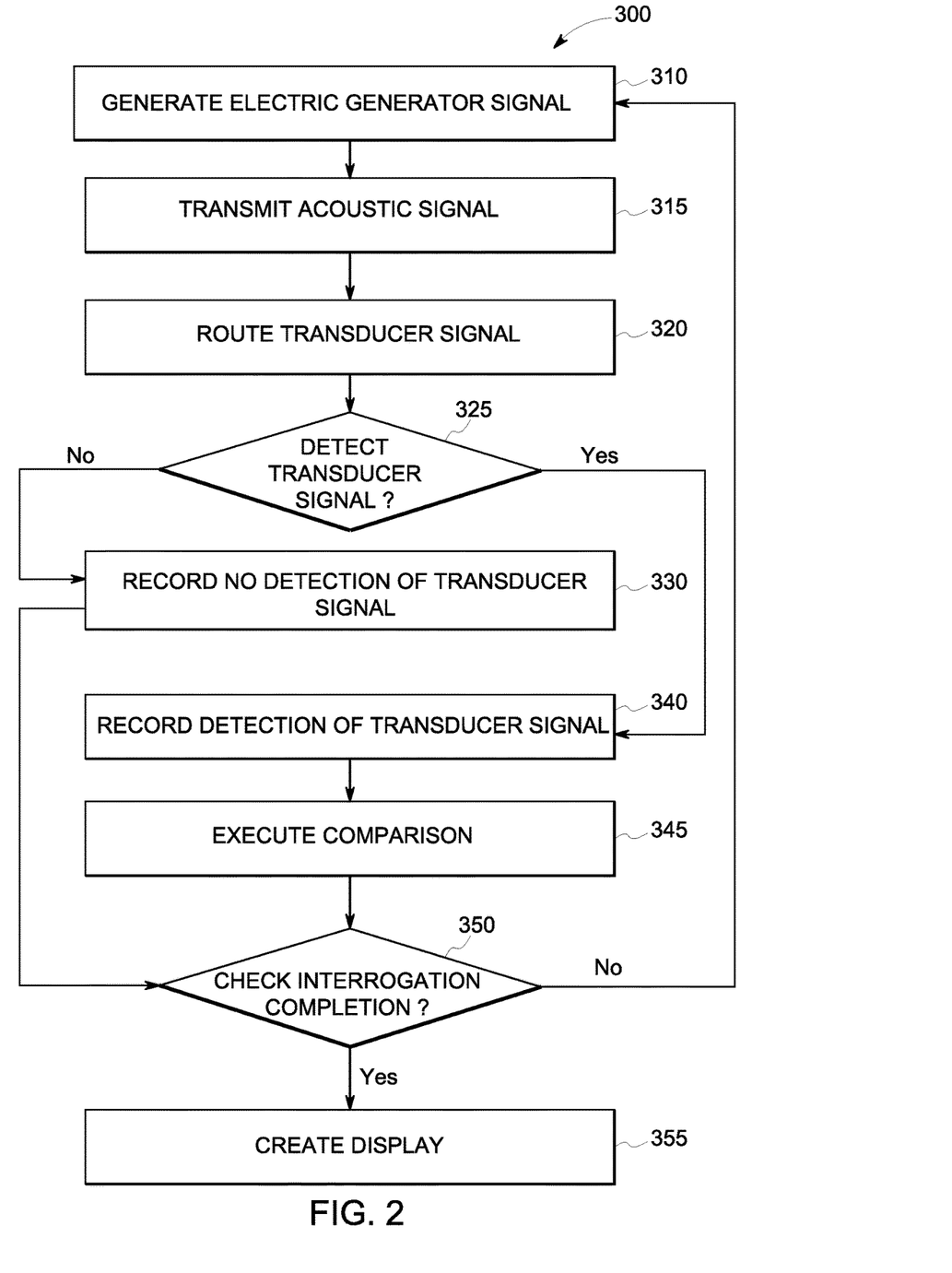
FIG. 2 shows a flow diagram illustrative of an example of a method of operating the system of FIG. 1 in accordance with the subject matter described herein.

Step 320 can include routing the operative connection of the receiver 130 with the selected transducer element(s) 110 of the acoustic probe 105. Step 325 can include determining if received transducer signal 195 is generated in response to acoustic signal 180. If the transducer element 110 is not functional or operational, step 330 can include recording not to detect receipt of the electrical transducer signal 195 from the selected electrical transducer(s) elements 110 in response to the transmission of the acoustic signal 180.

Step 340 can include detecting receipt and recording of the converted electrical transducer signal from operational or functional selected transducer elements 110 (generated in response to receipt of the acoustic signal 180) via the switch 200 from selected transducer elements 110 of the acoustic probe 105 for detection and measurement by the receiver 130. In cases where the transducer signal 195 is routed simultaneously from a subset group of the transducer elements 110, the subset group may correspond to a group of neighboring transducer elements 110. Step 335 can include executing a comparison of measured parameters of the received electrical transducer signals 195 to other interrogated transducer elements 110 of the acoustic probe 105 in calculating a functionality or operative ability of the selected transducer elements 110. For example, absence or significant deviation of the amplitude of the electrical transducer signal in comparison to other electrical transducer signals 195 from other interrogated transducer elements 110 can be indicative of the inoperability or non-functionality (e.g., associated with cracking or other damage to the piezoelectric crystal) of the respective transducer element 110.

Step 350 can include determining or performing a check if an interrogation of all the transducer elements 110 of the acoustic probe 105 has been completed. If completed, step 355 can include providing a display (described below) including illustrations indicative of the received converted electrical transducer signals 195 at the receiver 130, as well as the indication of the function or operability (e.g., pass versus fail) of the transducer elements 110 of the acoustic probe 105.

If interrogation of certain transducer elements 110 has not been completed, step 350 can further include prompting the user to select another of the series of transducer elements 110 of the acoustic probe 105 for interrogation or testing, and returning to step 310 until all of the transducer elements 110 of the acoustic probe 105 are interrogated.

Figure 3:
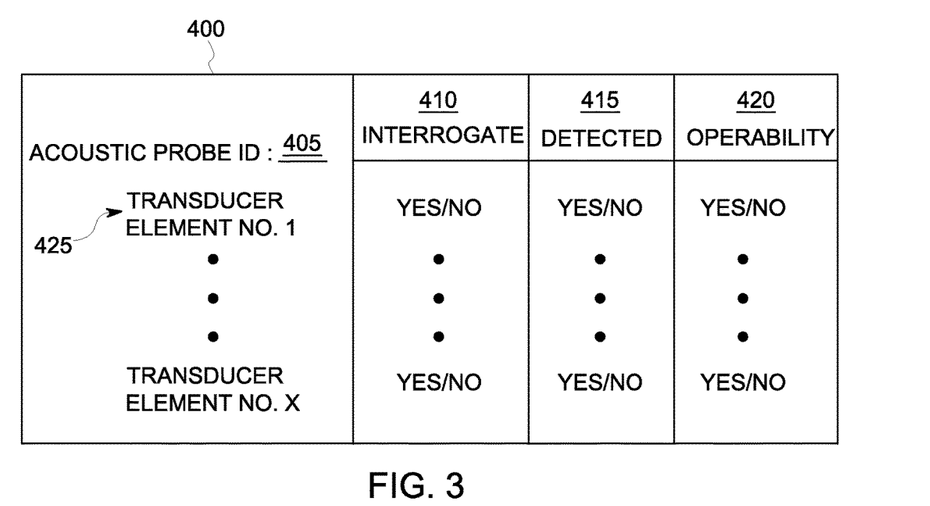
FIG. 3 shows schematic diagram illustrative of an example of a display generated by the system of FIG. 1 in accordance to the subject matter described herein.

FIG. 3 shows a schematic diagram of an example of a graphic display 400 in accordance to the subject matter described herein. The display 400 can provide illustrations indicative of an identifier 405 of the acoustic probe 105, a status of interrogation 410, a resultant responsive detection 415 of the transducer signal 195, and an indication or status of the operative ability 420 associated with identifiers 425 of each of the selected transducer element 110 of the acoustic probe 105 to convert between acoustic radiation and electrical signals in a required manner to perform imaging or other function.

Figure 4:
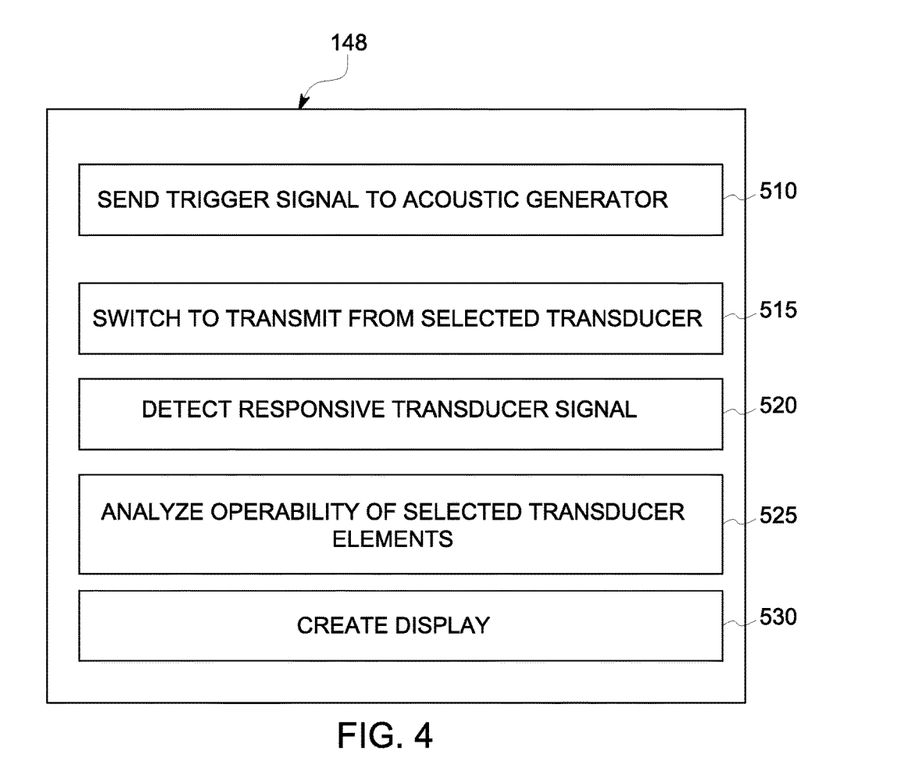
FIG. 4 shows a schematic diagram illustrative of a computer program product as shown in FIG. 1 in accordance to the subject matter described herein.

FIG. 4 illustrates an example of the computer program product 148 for execution by the processor 145 to operate the system 100 in executing the method 300 described above. The computer program product 148 can include a first module 510 of program instructions for execution sending a first electrical signal to the acoustic signal generator 125 to trigger sending the acoustic signal 180. A second module 515 can include program instructions for execution to selectively switch to receiver transmissions from selected transducer elements 110 of the acoustic probe 105. A third module 520 can include program instructions for execution in detecting receipt of the electrical transducer signal 195 via the switch 200 at the receiver 130 from each selected transducer element 110 of the acoustic probe 105. A fourth module 525 can include program instruction for execution in determining the operative ability of the selected transducer element 110 which can include comparing the electrical transducer signal 195 received from the selected transducer element 110 to another electrical transducer signal 195 received from another interrogated transducer element 110 of the acoustic probe 105. A fifth module 530 can include program instructions for creating the display 400 illustrative of the operative or functional ability (e.g., pass versus fail) of the selected transducer element 110 of the acoustic probe 105 to respond to the acoustic signal 180, for viewing by the user.

A technical effects of the subject matter described above can include, but is not limited to, providing the system 100 and method to test an operability of the acoustic probe 105 in a fast and yet repeatable manner. Another technical effect of the system 100 and method 300 is to provide for testing of the operability or functionality of the selected transducer elements 110 of the acoustic probe 105 without a need of cumbersome infrastructure (e.g., water tank, target) that enhances reduces cost, provides for mobility, and simplifies testing by the user.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

I claim:

1. System for testing an acoustic probe having a plurality of transducer elements adapted to convert between acoustic and electrical signals, the system comprising:
    an acoustic signal generator to send an acoustic signal into at least one of the plurality of transducer elements of the acoustic probe;
    a receiver having a switch to receive an electrical transducer signal from each selected transducer element of the acoustic probe, the electrical transducer signal generated in response to receipt of the acoustic signal at the selected transducer element;
    an analysis engine comprising computational circuitry configured to compare predefined parameters of the received electrical transducer signal from each selected transducer element relative to a threshold; and
    a display configured to provide an illustration indicative of an operative ability of the selected transducer element of the acoustic probe to convert between acoustic and electrical signals.

2. The system of claim 1, further comprising:
    an electrical signal generator connected to send a first electrical signal to the acoustic signal generator to trigger generating the acoustic signal.

3. The system of claim 1, the receiver having an analysis engine to compare the electrical transducer signal to at least one threshold.

4. The system of claim 1, wherein the acoustic signal generator is positioned against the acoustic probe so as to send the acoustic signal into the at least one of the plurality of transducer elements of the acoustic probe.

5. The system of claim 1, wherein the switch includes a matrix of integrated circuit boards to selectively route the electrical transducer signal from the selected transducer element of the acoustic probe.

6. The system of claim 1, wherein in response to not detecting the electrical transducer signal from the selected transducer element in response to communicating the acoustic signal to the acoustic probe, the receiver generates a display signal to trigger the illustration to indicate inoperability of the selected transducer element of the acoustic probe.

7. The system of claim 1, wherein in response to detecting the electrical transducer signal from the selected transducer element in response to communicating the acoustic signal to the acoustic probe, the receiver generates a display signal to trigger the illustration to indicate operability of the selected transducer element of the acoustic probe.

8. A method of testing an acoustic probe having a plurality of transducer elements adapted for conversion between acoustic and electrical signals, the method comprising the steps of:
    sending an acoustic signal into at least one of the plurality of transducer elements of the acoustic probe;
    detecting receipt of an electrical transducer signal via a switch at a receiver from each selected transducer element of the acoustic probe, the electrical transducer signal generated in response to receipt of the acoustic signal at the selected transducer element;
    analyzing predefined parameters of the received electrical transducer signal from each selected transducer element relative to a threshold; and
    displaying an indication of the operative ability of the selected transducer element of the acoustic probe to respond to the acoustic signal in response to the detecting step.

9. The method of claim 8, further comprising the step of:
    sending a first electrical signal to the acoustic signal generator to trigger sending the acoustic signal.

10. The method of claim 8, further comprising the step of:
    comparing the electrical transducer signal to at least one threshold.

11. The method of claim 8, further comprising the step of:
    locating the acoustic signal against the acoustic probe so as to send the acoustic signal into the at least one of the plurality of transducer elements of the acoustic probe.

12. The method of claim 8, further comprising the step of:
    selectively routing the electrical transducer signal from the selected transducer element of the acoustic probe through a switching relay on a circuit board to a measurement circuit.

13. The method of claim 8, wherein in response to not detecting the electrical transducer signal from the selected transducer element in response to communicating the acoustic signal to the acoustic probe, generating a display signal to trigger the illustration to indicate inoperability of the selected transducer element of the acoustic probe.

14. The method of claim 8, wherein in response to detecting the electrical transducer signal from the selected transducer element in response to communicating the acoustic signal to the acoustic probe, generating a display signal to trigger the illustration to indicate operability of the selected transducer element of the acoustic probe.

15. The method of claim 8, wherein the method does not use water to reflect the acoustic signal.

16. A non-transitory, tangible, computer-readable storage medium having a computer-readable program embodied therein for directing operation of an apparatus including an acoustic signal generator, a receiver having a switch, wherein the computer readable program includes instructions for operation in determining an operability of each of a plurality of transducer elements adapted for conversion between acoustic and electrical signals with respect to operation of an acoustic probe in accordance with the following:
    sending an acoustic signal into at least one of the plurality of transducer elements of the acoustic probe;
    detecting receipt of an electrical transducer signal via a switch at a receiver from each selected transducer element of the acoustic probe, the electrical transducer signal generated in response to receipt of the acoustic signal at the selected transducer element;

analyzing predefined parameters of the received electrical transducer signal from each selected transducer element relative to a threshold; and creating a display indicative of the operative ability of the selected transducer element of the acoustic probe to respond to the acoustic signal in response to the detecting step.

17. The computer readable storage medium of claim 16, further including instructions for operation in accordance with the following:

sending a first electrical signal to the acoustic signal generator to trigger sending the acoustic signal.

18. The computer readable storage medium of claim 16, wherein determining the operative ability of the selected transducer element includes comparing the electrical transducer signal received from the selected transducer element to another electrical transducer signal received from another transducer element of the plurality of transducer elements of the acoustic probe.

19. The computer readable storage medium of claim 16, wherein in response to not detecting the electrical transducer signal from the selected transducer element in response to communicating the acoustic signal to the acoustic probe, further including instructions for operation in accordance with:

generating a display signal to trigger the illustration to indicate inoperability of the selected transducer element of the acoustic probe.

20. The computer-readable storage medium of claim 16, wherein in response to detecting the electrical transducer signal from the selected transducer element in response to communicating the acoustic signal to the acoustic probe, further including instructions for operation in accordance with:

generating a display signal to trigger the illustration to indicate operability of the selected transducer element of the acoustic probe.

\* \* \* \* \*